United States Patent
Yang et al.

(10) Patent No.: US 7,893,466 B2
(45) Date of Patent: Feb. 22, 2011

(54) SEMICONDUCTOR FET SENSOR AND METHOD OF FABRICATING THE SAME

(75) Inventors: Jong Heon Yang, Daejeon (KR); In Bok Baek, Chungcheongbuk-do (KR); Chang Geun Ahn, Daejeon (KR); Chan Woo Park, Daejeon (KR); An Soon Kim, Daejeon (KR); Han Young Yu, Daejeon (KR); Chil Seong Ah, Daejeon (KR); Tae Youb Kim, Seoul (KR); Myung Sim Jun, Daejeon (KR); Moon Gyu Jang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 307 days.

(21) Appl. No.: 12/195,302

(22) Filed: Aug. 20, 2008

(65) Prior Publication Data

US 2009/0152596 A1 Jun. 18, 2009

(30) Foreign Application Priority Data

Dec. 13, 2007 (KR) ...................... 10-2007-0129581

(51) Int. Cl.
G01N 27/403 (2006.01)
(52) U.S. Cl. ................. 257/253; 257/414; 257/E21.04; 257/E29.166
(58) Field of Classification Search ................. 257/253, 257/414, E21.04, E29.166
See application file for complete search history.

(56) References Cited

U.S. PATENT DOCUMENTS

| | | | |
|---|---|---|---|
| 6,870,235 B2 | 3/2005 | Abstreiter et al. | |
| 7,557,002 B2 * | 7/2009 | Wells et al. | 438/238 |
| 2006/0054936 A1 | 3/2006 | Lieber et al. | |
| 2010/0055699 A1 * | 3/2010 | Kahya | 435/6 |
| 2010/0066348 A1 * | 3/2010 | Merz et al. | 324/71.1 |

FOREIGN PATENT DOCUMENTS

| | | |
|---|---|---|
| KR | 1020050081535 A | 8/2005 |
| KR | 1020060084735 A | 7/2006 |
| KR | 100758285 B1 | 6/2007 |

OTHER PUBLICATIONS

Eric Stern et al., "Label-free immunodetection with CMOS-compatible semiconducting nanowires", 2007 Nature Publishing Group, Nature vol. 445, Feb. 1, 2007, pp. 519-521.
Z. Li et al., "Sequence-Specific Label-Free DNA Sensors Based on Silicon Nanowires", 2004 American Chemical Society, Published on web Jan. 8, 2004, Nano Letters 2004, vol. 4, No. 2, pp. 245-247.

* cited by examiner

*Primary Examiner*—Fernando L Toledo

(57) ABSTRACT

Provided are a semiconductor Field-Effect Transistor (FET) sensor and a method of fabricating the same. The method includes providing a semiconductor substrate, forming a sensor structure having a fin-shaped structure on the semiconductor substrate, injecting ions for electrical ohmic contact into the sensor structure, and depositing a metal electrode on the sensor structure, immobilizing a sensing material to be specifically combined with a target material onto both sidewall surfaces of the fin-shaped structure, and forming a passage on the sensor structure such that the target material passes through the fin-shaped structure.

10 Claims, 9 Drawing Sheets

Si bulk

FIG. 7B

SiO$_2$
SiN
SiO$_2$
Si bulk

FIG. 7C

Fin

SiO$_2$
SiN
SiO$_2$
Si bulk

SEMICONDUCTOR FET SENSOR AND METHOD OF FABRICATING THE SAME

CROSS-REFERENCE TO RELATED APPLICATION

This application claims priority to and the benefit of Korean Patent Application No. 2007-129581, filed Dec. 13, 2007, the disclosure of which is incorporated herein by reference in its entirety.

BACKGROUND

1. Field of the Invention

The present invention relates to a Field-Effect Transistor (FET) sensor using semiconductor technology, and more particularly, to a semiconductor FET sensor employing a fin-shaped structure to improve sensitivity and a method of fabricating the FET sensor.

The present invention is derived from the work supported by the IT R&D program of the Ministry of Information and Communication and the Institute for Information Technology Advancement (South Korea) [Project Management Number: 2006-S-007-02. Project Title: Ubiquitous Health Monitoring Module and System Development].

2. Discussion of Related Art

A semiconductor FET sensor has a very small wire or thin film-type semiconductor structure to which a sensing material to be combined with a detection-target material is attached, and senses a change in electrical conductivity of the semiconductor structure when the target material is combined with the sensing material. The field effect is caused by an electrochemical reaction occurring when the target material is combined with the sensing material, or caused when an electrically charged target material is combined with the sensing material. In either case, electrons or holes of the semiconductor structure are accumulated or depleted due to the field effect, which may be measured by a change in conductivity. The above-mentioned FET sensor technology facilitates high-sensitivity detection and quantification of a target material in comparison with a conventional label-free sensor using color, fluorescence, etc.

Figure 1A:
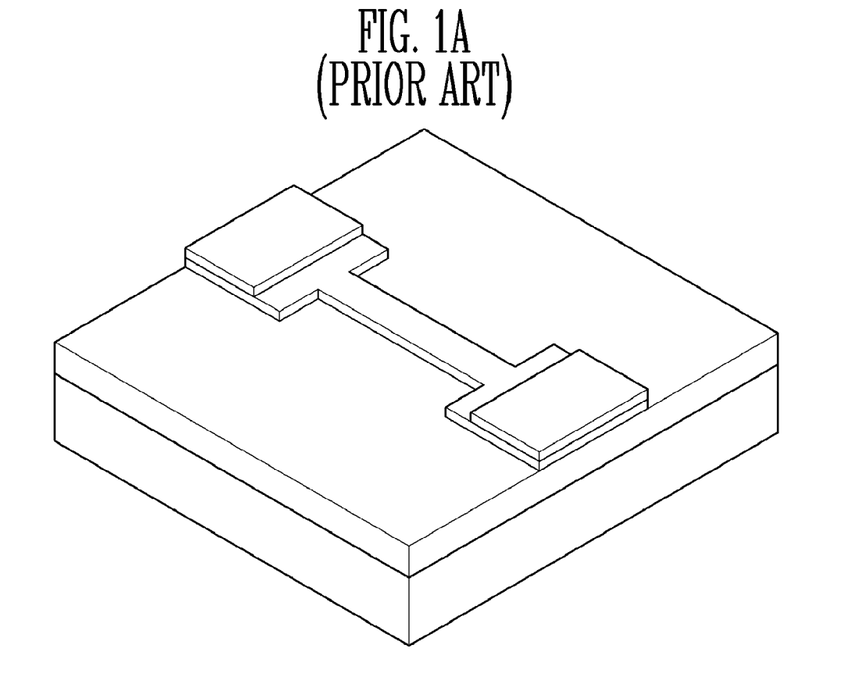
FIGS. 1A and 1B schematically show structures of typical Field-Effect Transistor (FET) sensors according to conventional art.
Figure 1B:
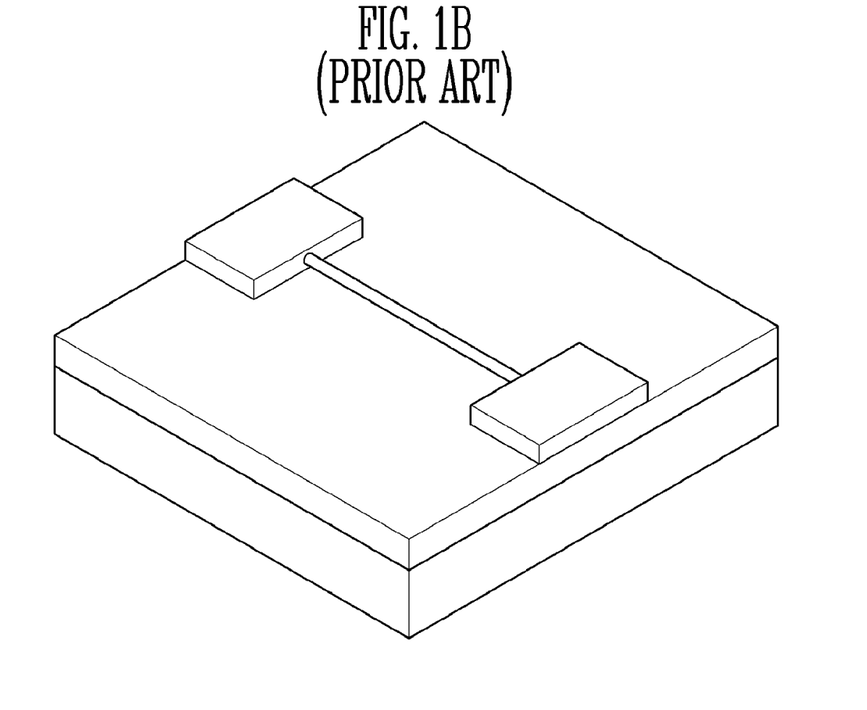

FIGS. 1A and 1B schematically show structures of typical FET sensors according to conventional art.

FIG. 1A shows an FET sensor having a gate region between a source and a drain to which a sensing material is attached. In the FET sensor having such a planar structure, the sensing material to be combined with a target material is disposed only in an upper part of the semiconductor structure. Thus, when a charged target material is combined with the sensing material, electrons or holes are accumulated or depleted in only one surface of the upper part.

FIG. 1B shows an FET sensor having a semiconductor structure in which a carbon nanotube or silicon nanowire is formed between a source and a drain. The FET sensor detects a target material using a change in conductivity of the carbon nanotube or silicon nanowire caused when a sensing material attached to the carbon nanotube or silicon nanowire is combined with the target material. Since a structure can be fabricated to have a size of 20 nm or less using a carbon nanotube or silicon nanowire, even a small amount of target material can cause enough depletion to enable high-sensitivity detection. However, such a carbon nanotube or silicon nanowire is made through chemical synthesis and thus is difficult to fix at a desired position on a sensor chip.

For the purpose of high-sensitivity detection of a target material, semiconductor structures of FET sensors on which a sensing material is combined with a target material need to be miniaturized. In a minute structure, a greater field effect is caused by a target material, and the level of a signal can increase. A semiconductor structure can be miniaturized by reducing a dimension such as a thickness of a thin film or a line width, and reducing the concentration of dopant in a substrate to reduce an interval between electrical depletions of a semiconductor structure. In reducing a dimension such as a thin-film thickness or line width of a semiconductor structure, the size of a semiconductor structure can only be reduced as far as current semiconductor process technology permits. A carbon nanotube or silicon nanowire synthesized by a Chemical Vapor Deposition (CVD) method can be miniaturized but is difficult to mass-produce. Use of a Silicon-on-Insulator (SOI) substrate enables mass-production, but limits miniaturization. For example, in SOI wafers currently used in mass-production lines, the uppermost silicon thin film is produced to a reduced thickness of 50 nm. An additional semiconductor process enables the thickness to be reduced to 20 nm but reduces process flexibility, thereby reducing production yield and increasing unit cost. In addition, the thinner an upper silicon layer of an SOI substrate, the larger an interface effect between the upper silicon layer and a Buried Oxide (BOX) layer. This affects the conductivity of the semiconductor structure, and reduces a Signal-to-Noise Ratio (SNR), thus deteriorating signal reproducibility. In addition, even when a target material is not combined with a sensing material, the semiconductor structure may already have been depleted by the interface effect, and current may not flow. Consequently, a signal may not be detected.

SUMMARY OF THE INVENTION

The present invention is directed to providing a fin-type semiconductor structure that has the same size as a planar structure according to conventional art but a larger surface area per unit cross-sectional area of a structure channel to cause more combining of a sensing material with a target material and thus improves the target material detection sensitivity of a Field-Effect Transistor (FET), and a method of fabricating the fin-type semiconductor structure.

The present invention is also directed to providing a method of fabricating the semiconductor structure using a low-priced bulk silicon substrate as well as an expensive Silicon-on-Insulator (SOI) wafer.

One aspect of the present invention provides a method of fabricating a semiconductor FET sensor, including: providing a semiconductor substrate; forming a sensor structure having a fin-shaped structure on the semiconductor substrate; injecting ions for electrical ohmic contact into the sensor structure, and depositing a metal electrode on the sensor structure; immobilizing a sensing material to be specifically combined with a target material onto both sidewall surfaces of the fin-shaped structure; and forming a passage on the sensor structure such that the target material passes through the fin-shaped structure.

Another aspect of the present invention provides a semiconductor FET sensor, including: a semiconductor substrate; a sensor structure having a fin-shaped structure formed on the semiconductor substrate, wherein ions for electrical ohmic contact are injected into the sensor structure and a metal electrode is deposited on the sensor structure; and a passage for allowing a target material pass through the fin-shaped structure, wherein, a sensing material to be specifically combined with the target material is fixed onto both sidewall surfaces of the fin-shaped structure.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Figure 2:
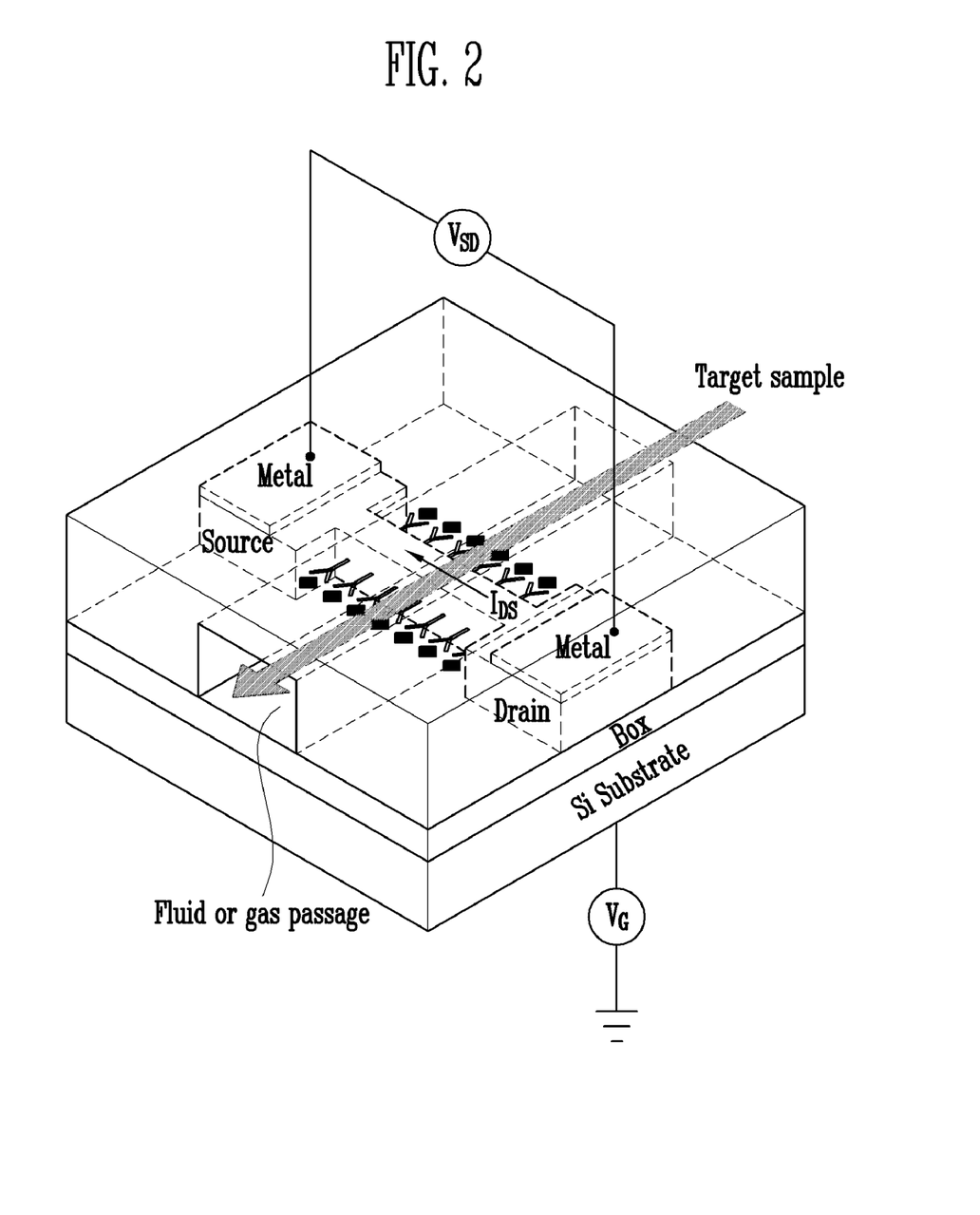
FIG. 2 is a perspective view of an FET sensor having a fin-shaped semiconductor structure according to an exemplary embodiment of the present invention.

FIG. 2 is a perspective view of a Field-Effect Transistor (FET) sensor having a fin-shaped semiconductor structure according to an exemplary embodiment of the present invention.

In a general FET sensor, an insulating layer is disposed on a substrate, and a sensor structure for sensing a target material is disposed on the insulating layer. As illustrated in FIG. 2, the FET sensor according to an exemplary embodiment of the present invention may employ a Silicon-on-Insulator (SOI) substrate in which a buried oxide (BOX) layer is disposed on a silicon substrate and a silicon thin film are disposed on the buried oxide layer, or a sensor structure in which a semiconductor thin film is disposed on an insulating substrate such as a glass or plastic substrate. The semiconductor thin film may be formed of polycrystalline silicon or amorphous silicon deposited at low temperature. To improve the detection sensitivity of the device, an appropriate gate bias is applied to a lower substrate, such that the electric conductivity of the sensor can be significantly changed by a change in charge caused by even a small amount of target material. To this end, an upper silicon substrate may be a single-crystal silicon thin film. In addition, a substrate capable of applying a bias to a bottom gate may be used as the lower substrate to facilitate depletion of carriers in an upper silicon channel or previously deplete carriers in the upper silicon channel. When a sensor is used in multifunctional products such as a display or a flexible material, it is difficult to employ a silicon bulk substrate as the lower substrate. To use an insulating substrate for multifunctional products, a bottom gate electrode may be previously formed on an insulator substrate, an insulating layer may be deposited again, and then amorphous silicon or polycrystalline silicon to be used as a sensor structure may be formed on the insulating layer.

The sensor structure is formed of a semiconductor, which may be silicon doped with an appropriate doping concentration. The impurity doping concentration may be about $10^{17}$ to $10^{19}$ $cm^{-3}$, and the impurity may include boron, phosphorus, arsenic, antimony, indium, and so on. Sides of the sensor structure correspond to a source and a drain, respectively. To form ohmic contacts, metal electrodes are formed after injecting contact ions using impurities having the same type as the sensor structure.

Appropriate voltage is applied between the source and the drain to measure a current as a change in conductivity caused by combining of a target material with a sensing material. The voltage applied between the source and the drain may be either of Direct Current (DC) voltage and Alternating Current (AC) voltage. A small AC voltage may be used to prevent damage to the target material and the sensing material. For example, an appropriate voltage may be several tens of mV to several hundreds of mV according to the resistance of the sensor. When an AC voltage is used, a lock-in amp may be used to improve sensitivity by removing ambient noise and increasing a Signal-to-Noise Ratio (SNR). Since the lock-in amp removes noise having a different frequency from an input signal and amplifies only a signal having the same frequency as the input signal, it can increase an SNR but is expensive equipment. To reduce the cost of a measurement terminal and miniaturize the measurement terminal, a signal may be detected by immobilizing an AC signal at the optimal frequency, adding a serial resistor, and then measuring the voltage of a sensor unit, instead of current.

A fin-shaped structure on which the target material is combined with the sensing material according to an exemplary embodiment of the present invention exists between the source and the drain. The sensing material for capturing the target material is fixed onto both sidewall surfaces of the fin-shaped structure. Here, the target material may include (1) a biomaterial such as glucose for measuring a blood-sugar level, which has the largest market size in the field of biosensors, a pregnancy hormone, a cancer cell, virus, cholesterol, DNA, and a biomarker such as a cancer marker, a Bovine Spongiform Encephalopathy (BSE) marker and a Cardiovascular Disease (CVD) marker, (2) an environmental material such as ecological hormone, Biochemical Oxygen Demand (BOD), heavy metals and agricultural chemicals, (3) a harmful material such as remaining agricultural chemicals included in food, antibiotics, germs and heavy metals, (4) a biochemical weapon used for mass destruction such as sarin and anthrax bacteria, and (5) microorganisms derived from biological fermentation processes, and specific chemical materials derived from chemical plants, oil refineries and drug companies. The sensing material corresponding to the target material may include an antibody, an enzyme, a receptor, and so on.

Perpendicular to the direction of the fin-shaped structure in which a current $I_{DS}$ flows between the source and the drain, a fluid or gas passage channel exists such that the target material passes through. The passage channel vertically crossing the fin-shaped structure has an empty inner space and is made of Poly-Dimethyl Siloxane (PDMS), acryl, Cyclic Olefin Copolymer (COC), and so on.

The FET sensor according to an exemplary embodiment of the present invention operates as follows. First, while a blood sample or buffer solution containing a target material, e.g., an antigen, passes through the fluid or gas passage channel disposed on the sensor structure, the target material is specifically combined with a sensing material, e.g., an antibody, fixed onto the fin-shaped structure. Here, the target material has a charge under a specific condition, and the field effect of the charge causes depletion or accumulation in the fin-shaped structure. This causes a change in conductivity between the source and the drain, and the change in conductivity is measured by a current detector. In this way, detection of the target material is performed.

Figure 3:
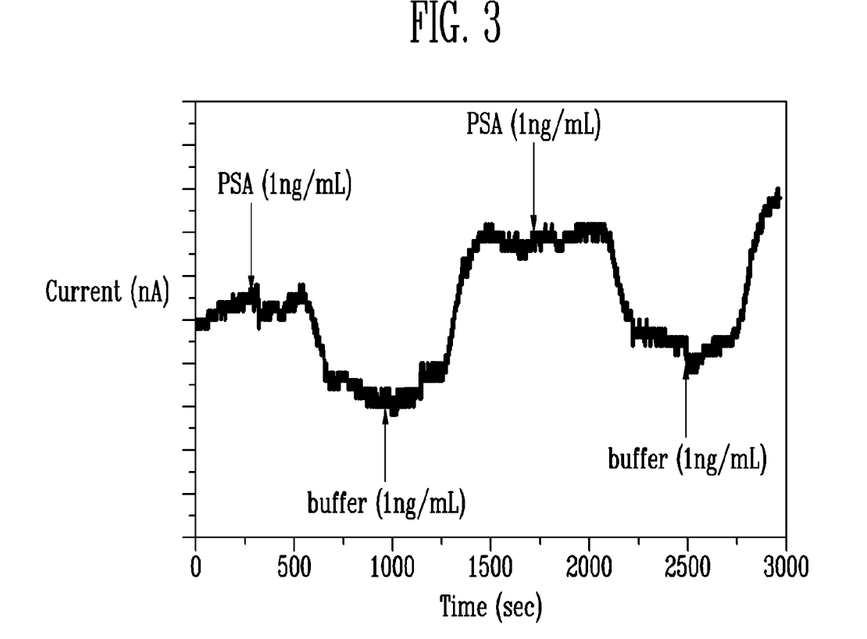
FIG. 3 is a graph illustrating an exemplary embodiment using a Prostate-Specific Antigen (PSA)

FIG. 3 is a graph illustrating an exemplary embodiment using a Prostate-Specific Antigen (PSA), which is a prostate cancer marker. According to the exemplary embodiment, when a buffer solution containing a PSA is flowed to a biosensor, it is combined with an anti-PSA fixed to the surface of the sensor, and a silicon channel is depleted by the field effect of a charge that the PSA has. Since depletion of the silicon channel causes a change in conductivity, the PSA may be detected using the change in conductivity. The PSA has a positive charge at a higher pH than an isoelectric point (pI) and a negative charge at a lower pH than the pI. When a buffer solution having a pH of 7.4 containing the PSA is flowed to a p-type silicon nanowire sensor, the PSA having a positive charge depletes hole carriers of a silicon nanowire channel, and thus conductivity decreases. When a buffer solution not containing the PSA is flowed, conductivity increases again.

Figure 4A:
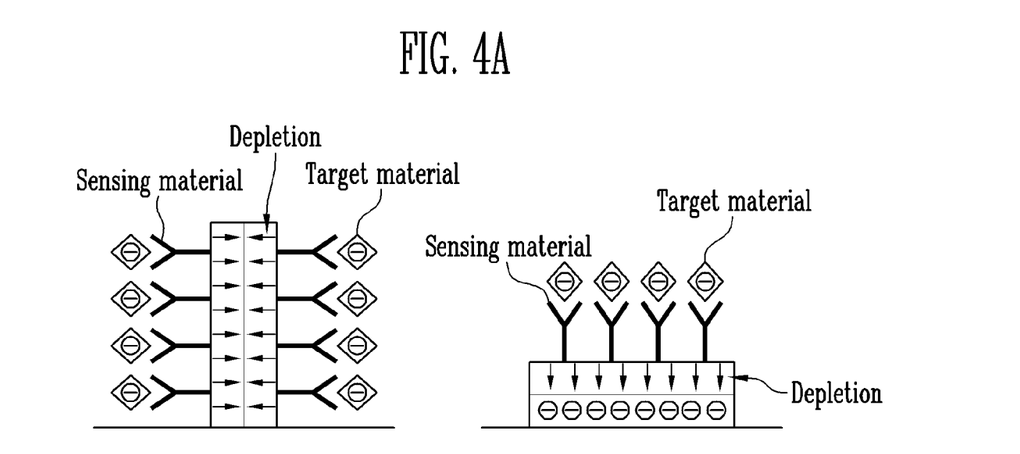
FIGS. 4A and 4B are conceptual diagrams and conductivity graphs of an FET sensor having a planar structure according to conventional art and an FET sensor having a fin-shaped structure according to an exemplary embodiment of the present invention.
Figure 4B:
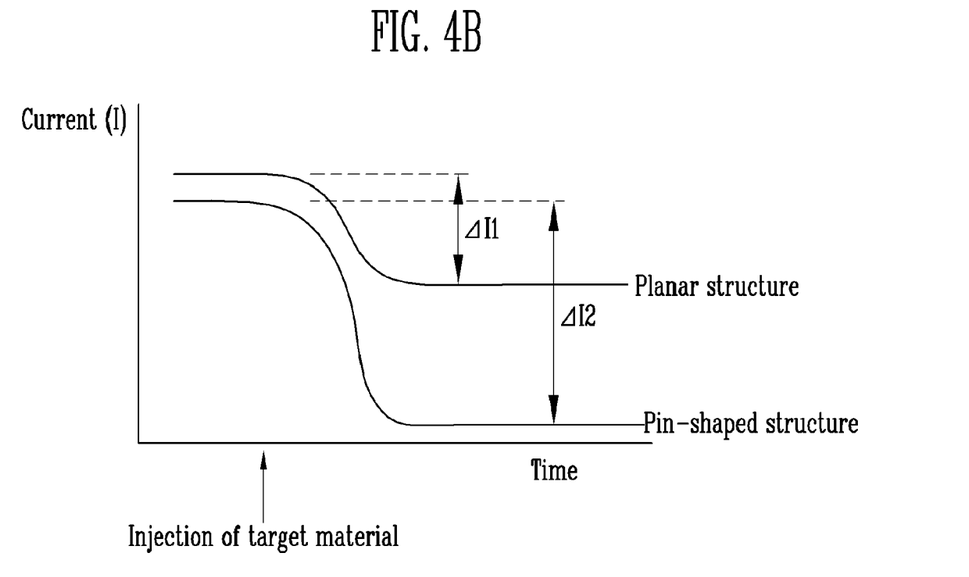

FIGS. 4A and 4B illustrate that an FET sensor having a fin-shaped structure according to an exemplary embodiment of the present invention can perform high-sensitivity detection of a target material in comparison with an FET sensor having a planar structure according to conventional art. As illustrated in FIG. 4A, a target material, e.g., an antigen, is combined with a sensing material, e.g., an antibody, only on the upper surface of the planar structure according to conventional art, and thus depletion occurs only to a specific depth. On the other hand, although the fin-shaped structure according to an exemplary embodiment of the present invention has the same size as the planar structure, a target material is combined with a sensing material on both sidewall surfaces of the fin-shaped structure, and thus it is possible to deplete the entire structure. Therefore, as illustrated in FIG. 4B, a decrease in conductivity of the fin-shaped structure caused by depletion is larger than that of the planar structure. When the planar structure is used according to conventional art, an upper silicon thin film may be formed thin, or the impurity concentration of a substrate may be lowered to deplete the entire channel and increase the level of a signal. However, it makes a semiconductor process complicated, so that the yield decreases. Also, a channel-base current is too low to detect a signal. In comparison with the planar structure, the fin-shaped structure with the same substrate doping concentration with that of the planar structure can use a thicker thin film and can cause a larger change in conductivity to improve detection sensitivity.

Figure 5A:
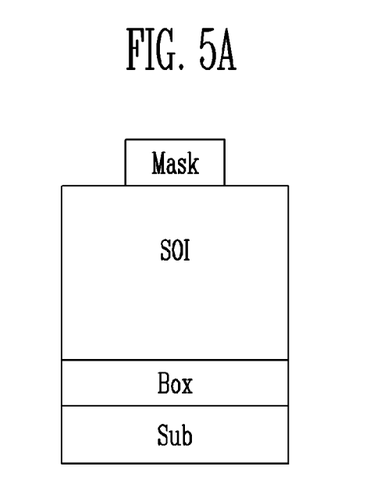
FIGS. 5A to 5C illustrate a method of fabricating a fin-shaped structure using a Silicon-on-Insulator (SOI) substrate according to an exemplary embodiment of the present invention.
Figure 5B:
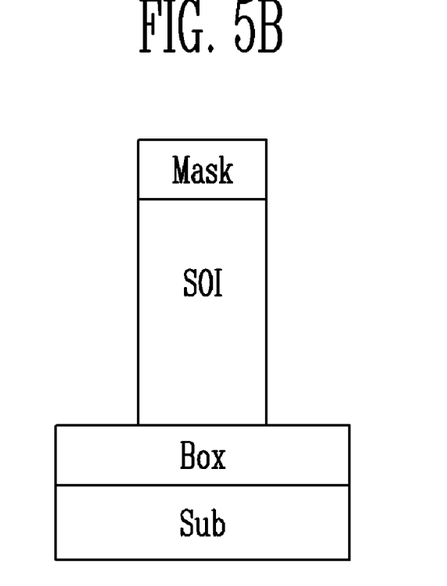
Figure 5C:
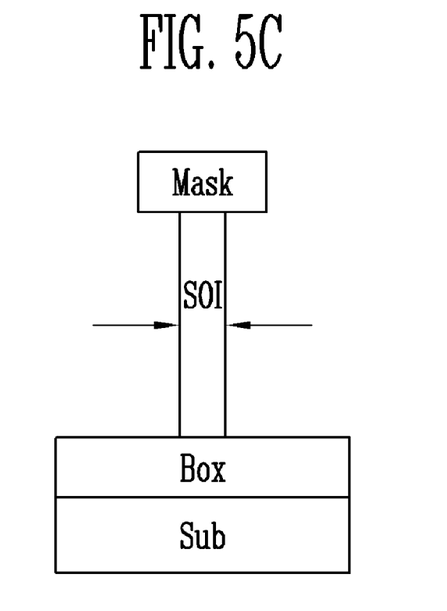

FIGS. 5A to 5C illustrate a method of fabricating a fin-shaped structure using an SOI substrate according to an exemplary embodiment of the present invention.

First, impurities are ion-injected into a prepared substrate such that a current of a detectable level can flow. Boron, indium, etc., are used as the injected impurities to form a p-type semiconductor having electron carriers, and phosphorus, arsenic, antimony, etc., are used to form an n-type semiconductor having hole carriers. An appropriate impurity doping concentration is about $10^{17}$ to $10^{19}$ cm$^{-3}$. After ion injection, an annealing process is performed to uniformly distribute the impurities to an appropriate depth.

Referring to FIG. 5A, a mask pattern is formed by a general lithography process. Here, a mask may be a photoresist, a silicon oxide layer or a silicon nitride layer. Referring to FIG. 5B, an upper silicon layer of an SOI is etched using the mask to form a fin-shaped structure. Here, a dry etching method or an anisotropic wet etching method may be used. Preferably, the anisotropic wet etching method, which does not damage a sidewall, is used for surface processing before immobilizing a sensing material. Silicon may be etched using a Tetramethylammonium Hydroxide (TMAH) or potassium hydroxide (KOH) solution to form a structure having an etched cross section like a fin. This is because an etching rate in the direction of a (100) or (110) plane is high, but an etching rate in the direction of a (111) plane is very low. Referring to FIG. 5C, when anisotropic wet etching is additionally performed after dry etching, or wet etching is additionally performed after anisotropic wet etching, the line width of the fin can be further reduced. When the line width of the fin is reduced, a change in conductivity of the sensor structure caused by depletion is more rapid, and thus the detection sensitivity of the target material can further increase.

Figure 5D:
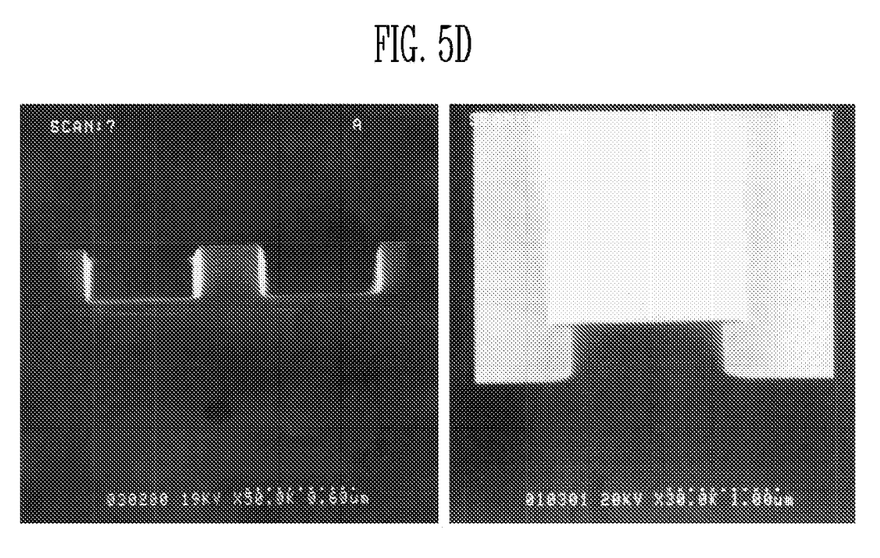
FIGS. 5D to 5F are scanning electron microscope images illustrating a process of fabricating the fin-shaped structure of FIGS. 5A to 5C.
Figure 5E:
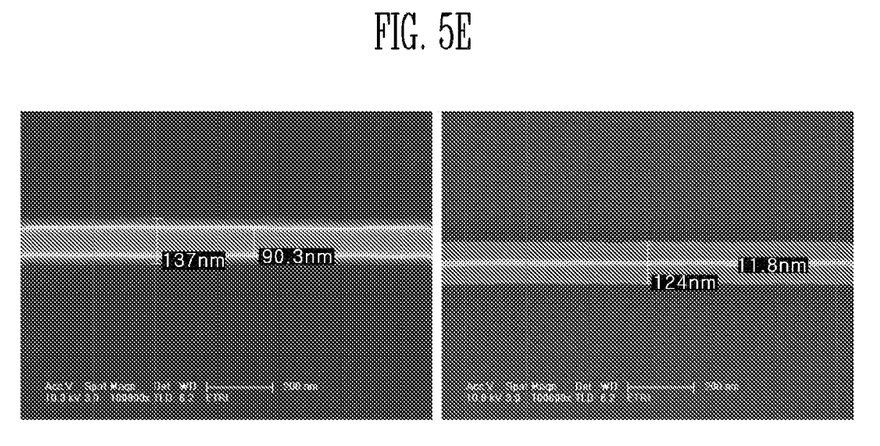
Figure 5F:
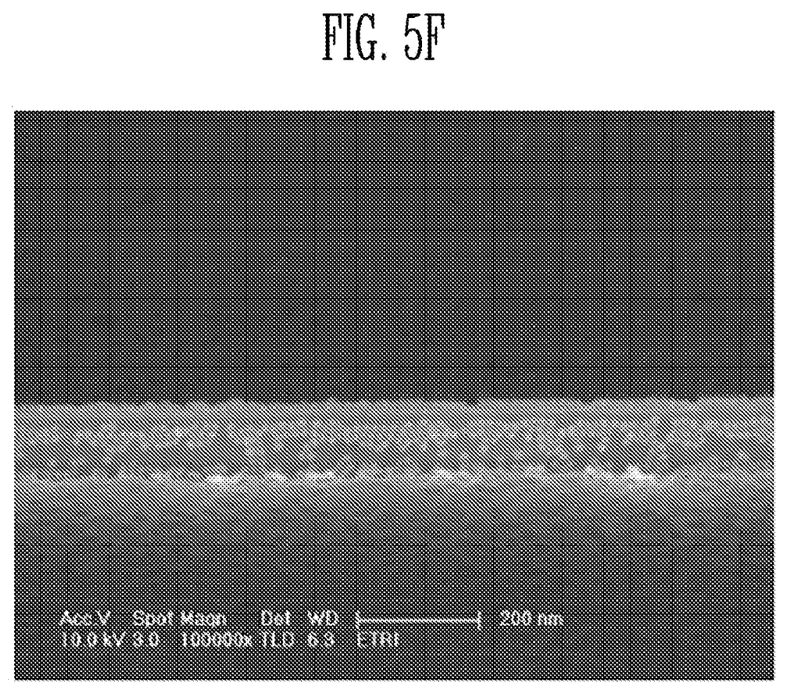

FIGS. 5D to 5F are scanning electron microscope images illustrating a process of fabricating the fin-shaped structures of FIGS. 5A to 5C.

Figure 5G:
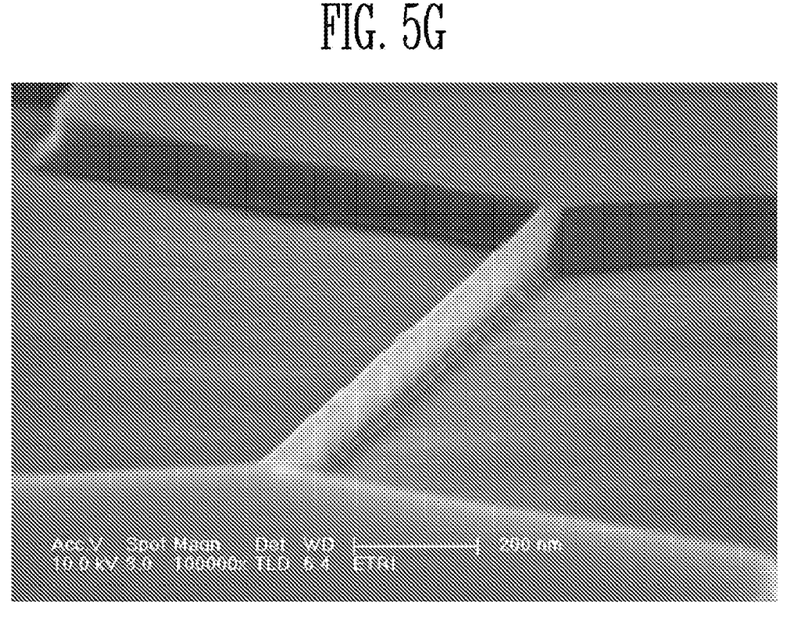
FIG. 5G is a scanning electron microscope image of a fin-shaped structure completed after a hard mask is removed.

FIG. 5D shows scanning electron microscope images of cross-sections of a silicon wafer having a (110) plane direction which is anisotropically wet-etched using a TMAH solution. FIG. 5E shows scanning electron microscope images of the silicon wafer which is additionally anisotropically wet-etched using a TMAH solution. In FIG. 5E, it can be seen that the line widths of a fin-shaped structure are reduced to 90 nm and 12 nm, which are much smaller than original mask sizes of 137 nm and 124 nm. Here, the height of the fin-shaped structure is 90 nm. The width of the fin-shaped structure may be 40 nm or less. When the concentration of dopant in a substrate is high, a carrier depletion area becomes relatively thin. Thus, the width of the fin-shaped structure may be further reduced. FIG. 5F shows a scanning electron microscope image of the fin-shaped structure fabricated using a (110) plane SOI substrate according to an exemplary embodiment of the present invention, on which a self-assembled monolayer for immobilizing a sensing material is deposited, and gold nanoparticles are attached using DNA to verify the self-assembled monolayer. Referring to FIG. 5F, it can be seen that the self-assembled monolayer for immobilizing a sensing material is deposited on a sidewall of the fin-shaped structure according to an exemplary embodiment of the present invention, like the planar surface of a planar structure. FIG. 5G is a scanning electron microscope image of a completed fin-shaped structure after a hard mask is removed, illustrating that it is possible to fabricate a fin structure having a line width of about 20 nm.

Figure 6A:
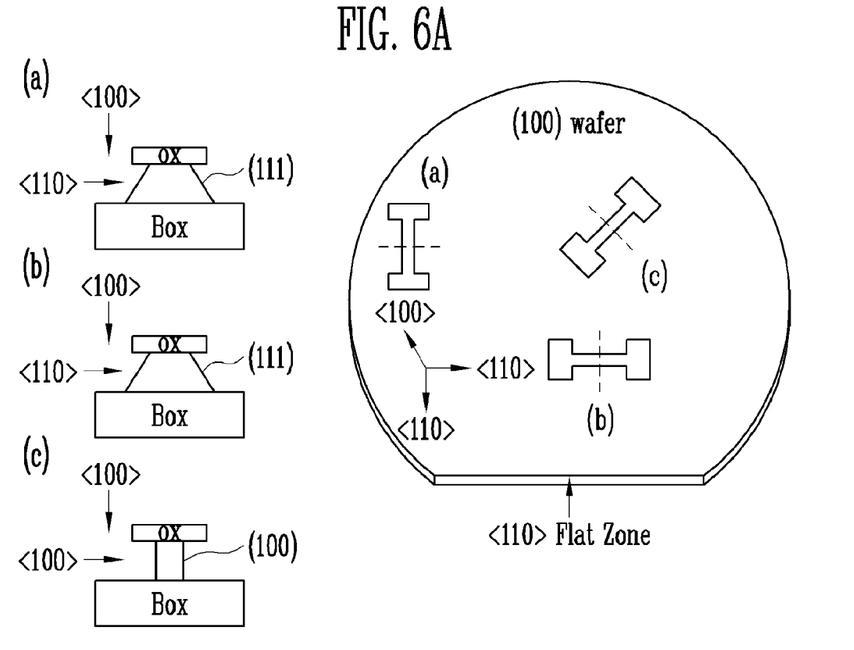
FIGS. 6A and 6B illustrate crystal directions of a wafer and fin directions in which a fin-shaped structure can be formed by an anisotropic wet etching method.
Figure 6B:
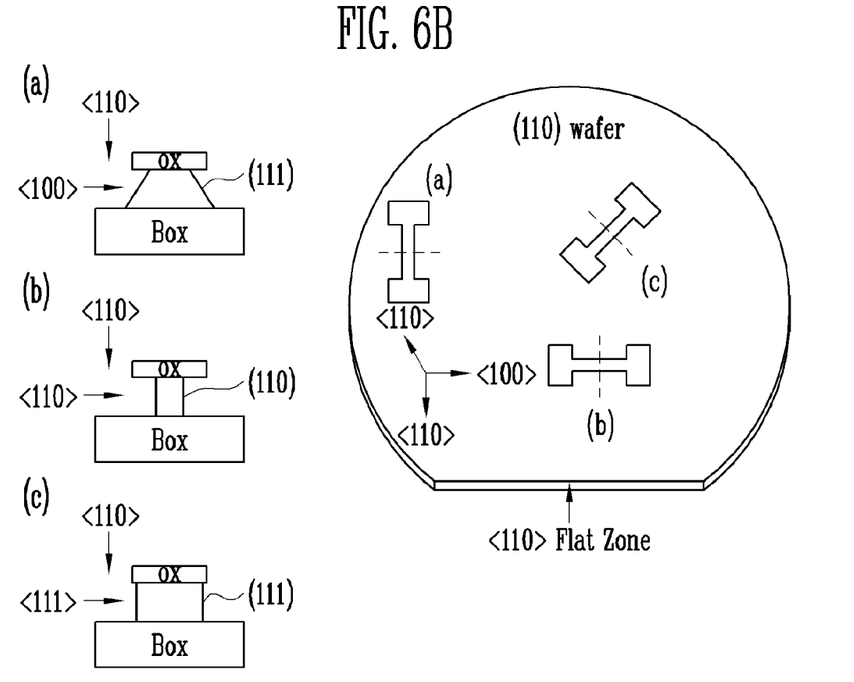

FIGS. 6A and 6B illustrate crystal directions of a wafer and fin directions in which a fin-shaped structure can be formed by an anisotropic wet etching method. Silicon etching rates using a TMAH solution are different according to plane directions, i.e., a silicon etching rate of a (100) plane is higher than that of a (110) plane, and the silicon etching rate of a (110)

plane is higher than that of a (111) plane. When a vertical etching rate is much higher than a horizontal etching rate, an anisotropic etching characteristic that a sidewall is perpendicular to upper and lower layers is exhibited. In addition, when a vertical etching rate is exactly the same as a horizontal etching rate, anisotropic etching is performed to form a sidewall perpendicular to upper and lower layers. In the latter case, etching is performed in a horizontal direction, and thus an undercut is formed inside an etch hard mask. In other cases, a sidewall having a slope is formed. As illustrated in FIG. 6A, when a silicon wafer substrate having a (100) plane is used, a fin structure having an undercut is formed in the case that etching is performed using a hard mask pattern of the fin in a direction tilted from a flat plane indicating a (110) direction by 45 degrees, and a sidewall having a slope is formed in the case that etching is performed in a direction parallel or perpendicular to the flat plane. On the other hand, as illustrated in FIG. 6B, when a silicon wafer substrate having a (110) plane is used, a fin structure having an undercut is formed in the case parallel to a flat plane, and a fin structure having no undercut is formed in the case tilted from the flat plane by 45 degrees. Therefore, to form the fin structure having a smaller line width by additional wet etching after the fin structure is etched, it is preferable to use a fin structure having a (110) plane as a sidewall rather than a (111) plane that is very slowly etched.

Figure 7A:
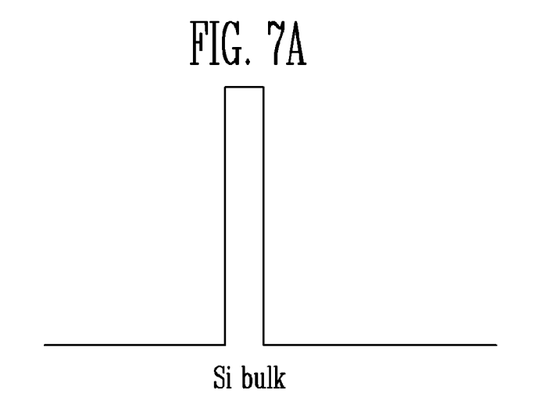
FIGS. 7A to 7C illustrate a method of fabricating a fin-shaped structure using a bulk substrate according to an exemplary embodiment of the present invention.
Figure 7B:
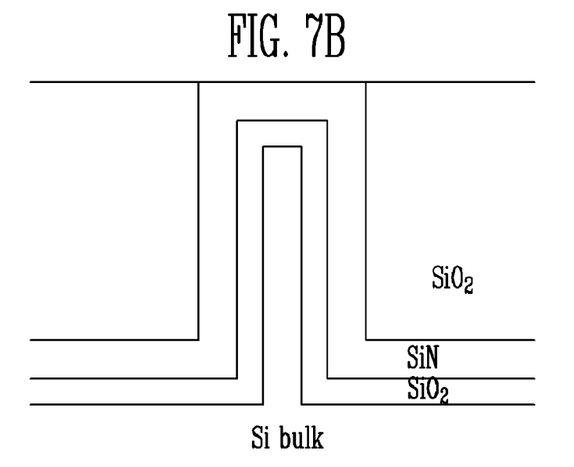
Figure 7C:
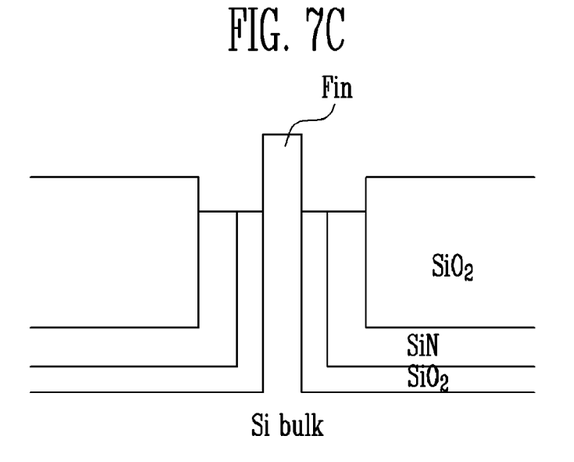

FIGS. 7A to 7C illustrate a method of fabricating a fin-shaped structure using a bulk substrate according to an exemplary embodiment of the present invention. First, impurities are ion-injected into a silicon bulk substrate once or at least two times such that a current having a detectable level can flow. Boron, indium, etc., are used as the injected impurities to form a p-type semiconductor having electron carriers, and phosphorus, arsenic, antimony, etc., are used to form an n-type semiconductor having hole carriers. An appropriate impurity doping concentration is about $10^{17}$ to $10^{19}$ cm$^{-3}$. After ion injection, an annealing process is performed to uniformly distribute the impurities to an appropriate depth. Unlike an SOI substrate having a BOX insulating layer, leakage current may flow through the lower substrate between a source and a drain in the silicon bulk substrate. To prevent the leakage current, impurities having an opposite type to a channel are first ion-injected under the channel such that a P-N junction or N-P junction is formed and the channel is electrically isolated.

Referring to FIG. 7A, a fin-shaped structure having a high aspect ratio is formed on a bulk substrate using a general lithography technique and an etching technique. The substrate may be a single-crystal silicon substrate, and a general dry etching technique or anisotropic wet etching technique may be used. Preferably, the anisotropic wet etching method, which does not damage a sidewall, is used for surface processing before immobilizing a sensing material. The width of the fin-shaped structure may be 40 nm or less, and vary according to the doping concentration of the substrate. For example, when the doping concentration of the substrate increases, the width of the fin-shaped structure must be reduced. Referring to FIG. 7B, an oxide insulating layer for protecting the surface is formed on the fin-shaped structure, a silicon nitride layer is deposited, and then a silicon oxide layer is thickly deposited to cover the entire fin-shaped structure. Subsequently, Chemical-Mechanical Polishing (CMP) is performed to planarize the silicon oxide layer and expose the silicon nitride layer on the fin-shaped structure. Referring to FIG. 7C, the silicon nitride layer and the silicon oxide layer deposited on the fin-shaped structure are etched to expose the fin-shaped structure, and thus the fin-shaped sensor structure employing a bulk substrate is completed.

Using a silicon bulk substrate, it is possible to fabricate an FET sensor at low cost in comparison with the case of using an expensive SOI substrate. Therefore, people can use the FET sensor to monitor their health in daily life.

Conventional FET sensors employ a planar structure, and thus a target material is combined with a sensing material on the upper surface alone. On the other hand, in a fin-shaped structure according to an exemplary embodiment of the present invention, a target material is combined with a sensing material on both sidewall surfaces. Therefore, depletion and accumulation of a channel is effectively adjusted, so that a high level signal can be obtained. In other words, an FET sensor having a fin-shaped structure according to an exemplary embodiment of the present invention can perform high-sensitivity detection of a target material in comparison with an FET sensor employing a conventional planar structure.

According to a sensor employing a planar structure, the thinner an upper silicon layer of an SOI substrate, the greater an interface effect between the upper silicon layer and a BOX layer. This affects the conductivity of the semiconductor structure and reduces an SNR, thereby deteriorating signal reproducibility. In addition, even when a target material is not combined with a sensing material, the semiconductor structure already has been depleted due to the interface effect. Therefore, a current may not flow, and a signal may not be detected. On the other hand, according to the sensor employing the fin-shaped structure, a small area contacts a BOX layer to reduce the interface effect. Thus, it is possible to increase signal reproducibility and sensitivity.

Anisotropic wet etching is used to implement a fin-shaped structure according to an exemplary embodiment of the present invention. Thus, defects of a structure surface can be reduced, and also it is possible to implement the fin-shaped structure to have a smaller width than that obtained through a general lithography technique. Consequently, the fin-shaped structure can operate as a high-sensitivity sensor.

A fin-shaped structure according to an exemplary embodiment of the present invention can be fabricated using a bulk substrate as well as an SOI substrate. When the bulk substrate is used, a BOX layer does not exist in a lower portion of the fin-shaped structure. Thus, no interface effect occurs, and an easier fabrication process is required in comparison with the case of using an SOI substrate. But most of all, since a bulk substrate less expensive than an SOI substrate is used, it is possible to produce low-priced and high-value-added semiconductor sensors.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A semiconductor Field-Effect Transistor (FET) sensor, comprising:
   a semiconductor substrate;
   a sensor structure having a fin-shaped structure formed on the semiconductor substrate, wherein ions for electrical ohmic contact are injected into the sensor structure and a metal electrode is deposited on the sensor structure; and
   a passage for allowing a target material pass through the fin-shaped structure, wherein, a sensing material to be specifically combined with the target material is fixed onto both sidewall surfaces of the fin-shaped structure.

2. The semiconductor FET sensor of claim 1, wherein the sensor structure is formed of polycrystalline silicon or amorphous silicon deposited on a glass or plastic insulating substrate, and the insulating substrate has a bottom gate electrode formed therein.

3. The semiconductor FET sensor of claim 1, wherein the sensor structure is formed of a Silicon-on-Insulator (SOI) substrate, and the sensor structure is formed by forming the SOI substrate on the semiconductor substrate, forming a mask pattern on the SOI substrate using a lithography process, and etching a silicon layer disposed on the SOI substrate using the mask.

4. The semiconductor FET sensor of claim 3, wherein the SOI substrate has a (100) or (110) plane direction, and the etching is performed by a dry etching method or an anisotropic wet etching method.

5. The semiconductor FET sensor of claim 4, wherein the fin-shaped structure is formed by additional anisotropic wet etching after the etching.

6. The semiconductor FET sensor of claim 1, wherein the sensor structure is formed of a bulk silicon substrate, and the sensor structure is formed by etching an upper portion of the bulk silicon substrate to form the fin-shaped structure having a high aspect ratio, forming an oxide insulating layer for protecting a surface on the bulk silicon substrate, depositing a silicon nitride layer on the oxide insulating layer, depositing a silicon oxide layer on the bulk silicon substrate to cover the entire surface of the fin-shaped structure, performing Chemical-Mechanical Polishing (CMP) to planarize the silicon oxide layer such that the silicon nitride layer is exposed on the fin-shaped structure, and etching the silicon nitride layer and the silicon oxide layer deposited on the fin-shaped structure to expose the fin-shaped structure.

7. The semiconductor FET sensor of claim 6, wherein the bulk silicon substrate has a (100) or (110) plane direction, and the etching is performed by a dry etching method or an anisotropic wet etching method.

8. The semiconductor FET sensor of claim 1, wherein one or more impurities selected from the group consisting of boron, phosphorus, arsenic, antimony and indium are ion-injected into the sensor structure at a concentration of $10^{17}$ to $10^{19}$ cm$^{-3}$.

9. The semiconductor FET sensor of claim 1, wherein a fin width of the fin-shaped structure ranges from 1 nm to 100 nm.

10. The semiconductor FET sensor of claim 1, wherein the passage in which a fluid or gas containing the target material can flow is formed on the fin-shaped structure using one of Poly-Dimethyl Siloxane (PDMS), acryl and Cyclic Olefin Copolymer (COC).

* * * * *